United States Patent
Ono (10) Patent No.: US 9,232,890 B2
(45) Date of Patent: Jan. 12, 2016

(54) OPHTHALMOLOGIC APPARATUS AND OPHTHALMOLOGIC IMAGING METHOD

(71) Applicant: CANON KABUSHIKI KAISHA, Tokyo (JP)

(72) Inventor: Mitsuhiro Ono, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 35 days.

(21) Appl. No.: 14/069,632

(22) Filed: Nov. 1, 2013

(65) Prior Publication Data

US 2014/0132928 A1 May 15, 2014

(30) Foreign Application Priority Data

Nov. 9, 2012 (JP) .................... 2012-247025

(51) Int. Cl.
*A61B 3/14* (2006.01)
*A61B 3/15* (2006.01)

(52) U.S. Cl.
CPC ...................... *A61B 3/152* (2013.01)

(58) Field of Classification Search
CPC ............. A61B 3/152; A61B 3/12; A61B 3/14
USPC ......................................................... 351/208
See application file for complete search history.

(56) References Cited

U.S. PATENT DOCUMENTS

| 2011/0051089 | A1* | 3/2011 | Wada et al. ................. 351/208 |
| 2011/0141436 | A1* | 6/2011 | Ono ............................ 351/206 |
| 2011/0228220 | A1 | 9/2011 | Kamada |
| 2012/0038886 | A1 | 2/2012 | Dobashi et al. |

FOREIGN PATENT DOCUMENTS

| CN | 102413757 A | 4/2012 |
| CN | 102438504 A | 5/2012 |
| JP | 62-34530 A | 2/1987 |
| JP | 07-327931 A | 12/1995 |
| JP | 08-275921 A | 10/1996 |
| JP | 11-178797 A | 7/1999 |
| JP | 2002-219107 A | 8/2002 |
| JP | 3569026 B2 | 9/2004 |
| JP | 2007-228994 A | 9/2007 |

OTHER PUBLICATIONS

Feb. 28, 2015 Chinese Official Action in Chinese Patent Appln. No. 201310549550.4.

* cited by examiner

*Primary Examiner* — Mahidere Sahle
(74) *Attorney, Agent, or Firm* — Fitzpatrick, Cella, Harper & Scinto (57) ABSTRACT

In order to prevent inaccurate position detection caused by overlapping between a position alignment index and an optic papilla of a fundus in position alignment between an eye to be inspected and an apparatus when a fundus image is photographically captured, an ophthalmologic apparatus includes: a projection unit configured to project a plurality of alignment indices onto an eye to be inspected; an optic papilla position detection unit configured to detect an optic papilla position of the eye to be inspected; and an alignment detection unit configured to detect a positional relation between the eye to be inspected and an apparatus main body from a reflection image of the alignment index, wherein the alignment detection unit performs alignment detection by selecting a reflection image of at least one of the reflection images of the plurality of alignment indices depending on the optic papilla position.

14 Claims, 6 Drawing Sheets

| LEFT/RIGHT | FIXATION TARGET POSITION | OPTIC PAPILLA POSITION |
|---|---|---|
| LEFT | 0, 0 | 180, 200 |
| LEFT | 0, 1 | 180, 205 |
| ⋮ | ⋮ | ⋮ |
| LEFT | 3, 3 | 200, 240 |
| ⋮ | ⋮ | ⋮ |
| LEFT | 7, 3 | 300, 240 |

OPHTHALMOLOGIC APPARATUS AND OPHTHALMOLOGIC IMAGING METHOD

BACKGROUND OF THE INVENTION

1. Field of the Invention

The present invention relates to an ophthalmologic apparatus and an ophthalmologic imaging method.

2. Description of the Related Art

As an ophthalmologic apparatus, there are widely known a fundus camera that photographically captures a fundus of an eye to be inspected. In addition, as the fundus camera, there is known an apparatus that observes the eye to be inspected using a plurality of imaging modes, such as color angiography, visible fluorescent angiography (FAG), or near-infrared indocyanine green (ICG) video angiography, in order to capture an image depending on a purpose of the examination.

When the fundus camera is used to capture an image, it is necessary to delicately adjust a working distance between the eye to be inspected and the fundus camera. Therefore, an alignment index is projected onto the eye to be inspected, and alignment adjustment is performed using the index image.

In Japanese Patent Application No. S62-34530, there is proposed a fundus camera in which the alignment index is projected onto a cornea of the eye to be inspected in order to determine whether or not an alignment position is appropriate in a focus state on an alignment image that is a reflection image of the index.

In addition, in Japanese Patent No. 3569026, there is proposed a fundus camera that automatically detects the alignment index, and performs imaging by adjusting an apparatus position.

When the fundus image is photographically captured, an optic papilla of the eye to be inspected is visualized brightly. It was recognized that the optic papilla overlaps with the alignment index depending on an orientation of the eye to be inspected when the alignment is detected. As a result, it is difficult to accurately detect the alignment index. If the alignment index is not accurately detected, a flare is easily mixed into the fundus image due to reflection light of an illumination light beam at a cornea or a lens.

SUMMARY OF THE INVENTION

In view of the aforementioned problems, the invention provides an ophthalmologic apparatus capable of accurately detecting an alignment index regardless of an orientation of an eye to be inspected to automatically perform imaging or automatically adjust the alignment index.

In order to address the problems described above, an ophthalmologic apparatus according to the present invention includes: a projection unit configured to project a plurality of alignment indices onto an eye to be inspected; an optic papilla position detection unit configured to detect an optic papilla position of the eye to be inspected; and an alignment detection unit configured to detect a positional relationship between the eye to be inspected and an apparatus main body from a reflection image of the alignment index, wherein the alignment detection unit performs alignment detection by selecting at least one of the reflection images of the plurality of alignment indices depending on the optic papilla position.

In order to address the problems described above, an ophthalmologic imaging method according to the present invention includes: projecting a plurality of alignment indices onto an eye to be inspected; detecting an optic papilla position of the eye to be inspected; and detecting a positional relationship between the eye to be inspected and an apparatus main body from a reflection image of the alignment index, wherein, in the detecting of the positional relationship, alignment is detected by selecting a reflection image of at least one of the reflection images of the plurality of alignment indices depending on the optic papilla position.

According to the invention, it is possible to accurately detect the alignment index regardless of the orientation of the eye to be inspected automatically perform imaging, and automatically adjust the alignment index.

Further features of the present invention will become apparent from the following description of exemplary embodiments (with reference to the attached drawings).

DESCRIPTION OF THE EMBODIMENTS

Preferred embodiments of the present invention will now be described in detail in accordance with the accompanying drawings.

First Embodiment

Figure 1:
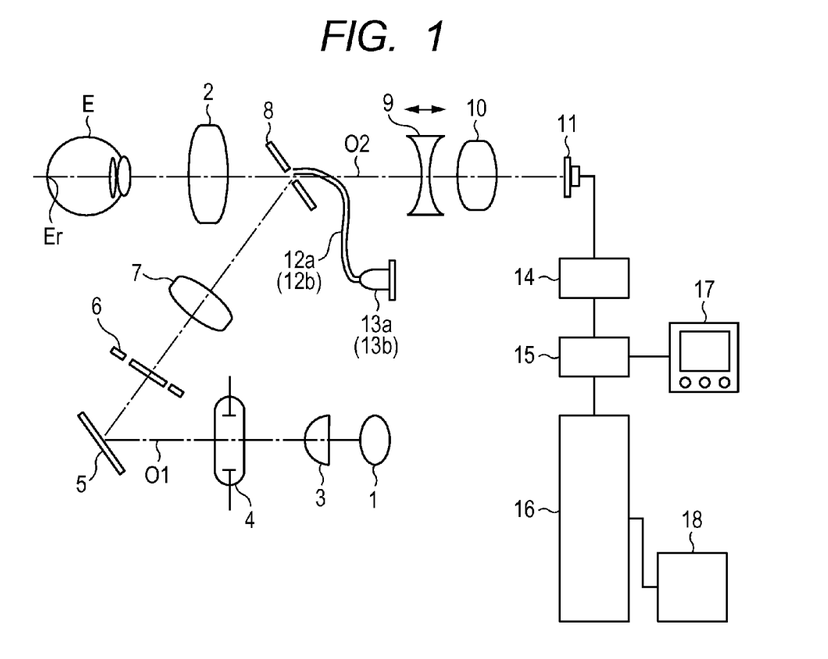
FIG. 1 is a diagram illustrating a configuration of an ophthalmologic photographing apparatus according to First embodiment.

FIG. 1 is a diagram illustrating a configuration of a fundus camera that is an ophthalmologic apparatus according to a first embodiment of the invention. On an optical path O1 from an observation light source 1 to an objective lens 2 positioned in front of an eye to be inspected E, the observation light source 1, a condenser lens 3, a photographing light source 4, and a mirror 5 are arranged. Moreover, in a reflection direction of the mirror 5, an aperture 6 having a ring-shaped opening, a relay lens 7, and a perforated mirror 8 are sequentially arranged to configure a fundus illumination optical system. In addition, the observation light source includes an LED light source that emits near-infrared light.

On an optical path O2 behind the perforated mirror 8, a focus lens 9, a photographic lens 10, and an image pickup element 11 including, for example, a CCD, are sequentially arranged to constitute a fundus photographing optical system.

In addition, at a position deviated in a horizontal direction from the optical path O2 in the vicinity of a cavity of the perforated mirror 8, an emission end of a light guide 12a configured to guide an index light beam is disposed. An LED light source 13a for illuminating an alignment index is connected to an incident end of the light guide 12a.

At a symmetric position with respect to the optical path O2 of the emission end of the light guide 12a, an emission end of a light guide 12b is disposed. A light-emitting diode (LED) light source 13b (not illustrated) having the same wavelength as the LED light source 13a is connected to the incident end of the light guide 12b. In this way, an alignment index projection optical system is configured.

An output of the image pickup element 11 is connected to a system control section 16 that controls an entire fundus camera through an accumulated charge reading section 14 and an image signal processing section 15. Furthermore, a display section 17 configured to display a captured image is connected to the image signal processing section 15. In addition, a manipulation section 18 configured to manipulate the system control section 16 and the ophthalmologic apparatus from the outside is connected to the system control section 16.

When the fundus is observed, illumination light emitted from the observation light source 1 passes through the condenser lens 3 and the photographing light source 4 and is reflected on the mirror 5. Reflection light reflected on the mirror 5 passes through the aperture 6 and the relay lens 7, is reflected on a peripheral portion of the perforated mirror 8, and irradiates a fundus Er of an eye to be inspected E via the objective lens 2. Reflection light of the fondue Er passes through the objective lens 2, the cavity of the perforated mirror 8, the focus lens 9, and the photographic lens 10, forms an image on an imaging surface of the image pickup element 11, and is observed as a fundus image.

An index light beam emitted from the emission ends of the light guides 12a and 12b from the LED light sources 13a and 13b is projected onto the eye to be inspected E as alignment indices Pa and Pb via the objective lens 2. When a working distance between the eye to be inspected E and the fundus camera is appropriate, a reflection image of the index light beam that is reflected on a corneal surface of the eye to be inspected E becomes parallel light, passes through the same optical path as that of the fundus reflection light of the illumination light beam, and forms an index image on the imaging surface of the image pickup element 11.

The accumulated charge reading section 14 maintains an accumulated charge after photoelectric conversion of the image pickup element 11, reads the accumulated charge, reads a signal while the maintained charge is continuously cleared, and outputs the signal to the image signal processing section 15.

In addition, when the image signal processing section 15 is in an observation mode under control of the system control section 16, an observation mode process is performed. That is, when observation is performed, the image signal processing section 15 electronically adds an alignment mark M serving as a guide of the working distance between the eye to be inspected E and the fundus camera to the fundus image by the accumulated charge of the image pickup element 11, and outputs the observation image to the display section 17.

Figure 2:
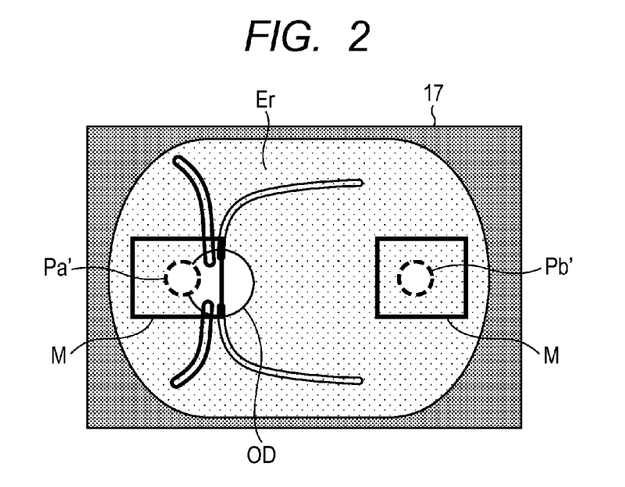
FIG. 2 is a schematic diagram illustrating an image when a fundus is observed.

FIG. 2 is a schematic diagram illustrating an image when the fundus is observed. When the fundus is observed, a fundus image Er' illuminated by the observation light source 1, the alignment mark M, and alignment index images Pa' and Pb' at the corneal surface due to the alignment indices Pa and Pb are displayed on the display section 17. An operator manipulates a stage portion that can move the entire optical portion of the fundus camera illustrated in FIG. 1 such that the index images Pa' and Pb' enter the alignment mark M, and the working distance between the eye to be inspected E and the fundus camera is adjusted.

In this case, an operator manipulates the focus lens 9 to perform focus adjustment using reflection light of the focus index (not illustrated) projected onto the fundus Er.

Next, an image processing section configured to detect an alignment state between the eye to be inspected and an apparatus main body will be described. In this embodiment, an image processing configuration configured to detect whether or not alignment with the eye to be inspected is appropriate will be described.

As described above, in order to adjust alignment between the eye to be inspected and the apparatus, an operator manipulates the stage portion. In the meantime, the image processing section determines the alignment state based on the fundus image and notifies the result to an operator.

The image processing section is embedded in the system control section 16. The fundus image processed by the image signal processing section 15 is sequentially obtained from system control to perform an image processing.

Figure 3:
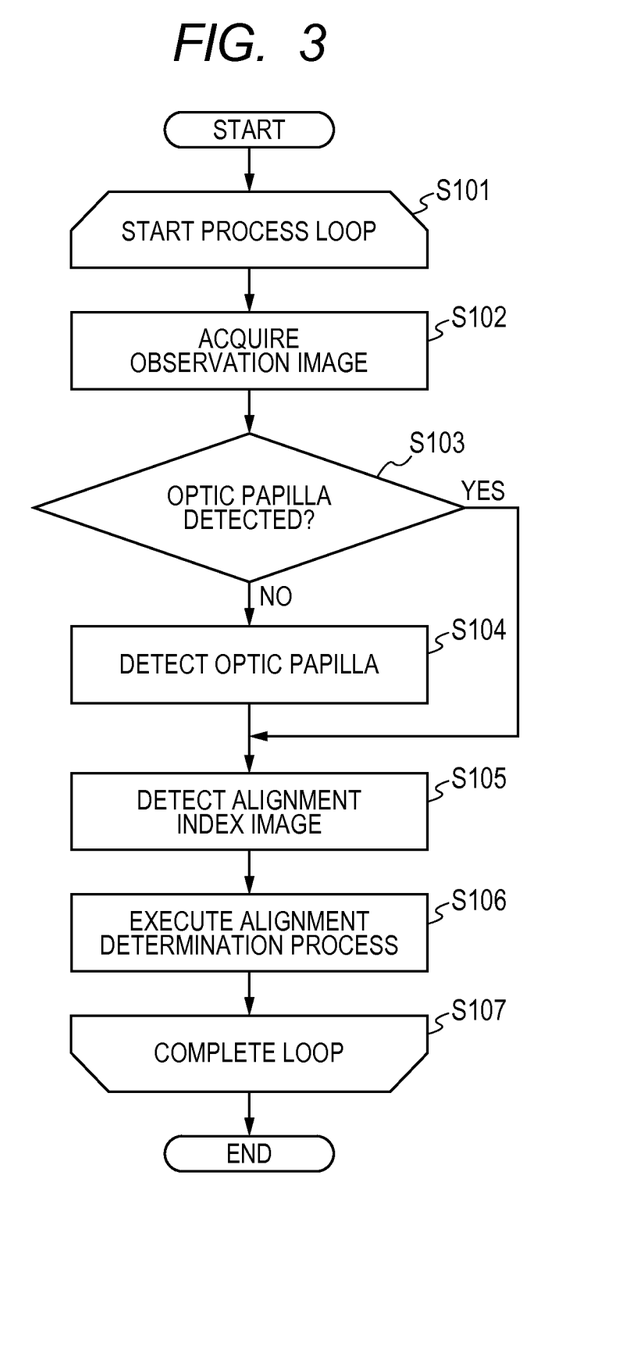
FIG. 3 is a flowchart illustrating an image processing of an alignment detection section according to First embodiment.

FIG. 3 illustrates an image processing flow of an alignment detection section. In step S101, a process loop starts. First, in step S102, the fundus image processed by the image signal processing section 15 is acquired as an observation image.

Then, it is determined whether or not an optic papilla has been detected (step S103). When the optic papilla has not been detected, the optic papilla is detected in the following step 104. After the detection, the process advances to step 105.

When the optic papilla is not detected, the LED light source 13 may be turned off. In this case, since there is no alignment index image, it is difficult to perform the following alignment index detection. However, the optic papilla may be easily extracted. In this case, after the optic papilla is detected, the LED light source 13 is turned on again, and the alignment index is detected. According to the invention, the LED 13 or the like serves as a projection unit that projects a plurality of alignment indices onto the eye to be inspected. In addition, the projection unit exemplified in the present embodiment may have various modifications as necessary.

In step S104, the optic papilla is detected from the observation image. Since the optic papilla is visualized brightly in the fundus image, a bright part of the fundus image is extracted and is set as the optic papilla. Extraction and position detection of the optic papilla from the fundus image are performed by a module that serves as an optic papilla position detection unit in the image processing section. In addition, when alignment is significantly deviated, the optic papilla is not visualized in the fundus image or is viewed significantly dark even if it is visualized. In this case, the process is terminated by assuming that the optic papilla part is not detected.

In this step, the process skips when the optic papilla is detected. However, considering that eye movement of the examinee is not stable, the process may be performed each time. In addition, when the optic papilla is stably detected in a plurality of fundus images, the process may skip by assuming that the eye movement of the eye to be inspected is stable.

Then, the alignment index images Pa' and Pb' are detected (step S105). Since the alignment index images Pa' and Pb' are also observed as bright spots in the observation image, it is possible to detect the alignment index image by extracting when there is a bright part. According to this embodiment, since two alignment indices are projected, two maximum index images are detected. However, when the alignment is deviated, one or no image may be detected.

Then, an alignment state is determined based on the detected alignment index image (step S106). In alignment determination, a positional relationship between the eye to be inspected and the apparatus is three-dimensionally detected. A horizontal direction of the eye to be inspected and the apparatus is set to as an X direction, a vertical direction is set to as a Y direction, and a direction connecting the eye to be inspected and the apparatus is set to as a Z direction. When two-dimensional positions of the alignment index images Pa' and Pb' are detected in the image, it is possible to detect alignment in the X and Y directions. When contrasts of indices of Pa' and Pb' are detected, it is possible to detect alignment in the Z direction. When this three-dimensional positional relationship between the eye to be inspected and the apparatus is completely within a predetermined range, the alignment is completed. The process of determining the alignment state in step S106 is performed by a module serving as an alignment detection unit configured to detect a positional relation between the eye to be inspected and the apparatus main body from the reflection image of the alignment index in the image processing section.

The alignment determination may be performed on each of the alignment index images Pa' and Pb'. However, in a positional relationship in which the optic papilla overlaps with the alignment index images Pa' and Pb', it is difficult to accurately detect the alignment index. In FIG. 2, the alignment index Pa' partially overlaps with the optic papilla OD. In this case, it is difficult to detect an XY position of the alignment index Pa' used for detecting the XY direction of the eye to be inspected and the apparatus. Particularly, it is difficult to detect a contrast of the alignment image used for detecting the Z direction.

Therefore, when the optic papilla position detected in step S104 and the alignment index image position detected in step S105 are adjacent to each other, an alignment determination result of an alignment index image in an adjacent side is not used, but a determination result of the alignment index image in a non-adjacent side is used. Here, the optic papilla may be positioned in the center portion of the observation image and may not be adjacent to either of the alignment indices Pa' or Pb'. In this case, only when alignment of both the alignment index images Pa' and Pb' is completed, it is determined that the alignment is completed. Alternatively, a single result of any alignment index image may be used. That is, the alignment detection unit may select at least one of reflection images of a plurality of alignment indices depending the optic papilla position and detect alignment using the selected image. Alternatively, a measurement time may be considered by increasing the number of alignment index images, and then, alignment accuracy may increase.

The alignment determination result is notified to the image signal processing section 15 and is displayed on the display section 17. Based on t e alignment result, an operator performs shooting to capture an appropriate image. As a result, it is possible to photograph the fundus image with higher alignment accuracy.

Second Embodiment

In this embodiment, instead of the papilla detection unit of the first embodiment configured to automatically detect the papilla, an ophthalmologic examination apparatus has a left/right eye detection unit configured to detect which of the right eye or the left eye is to be inspected and estimates a papilla position from the left/right eye to be inspected.

In this embodiment, before fundus examination, which of the right eye and the left eye is the eye to be inspected is set using the manipulation section 19 connected to the system control section 16.

Alternatively, which of the right eye or the left eye is set to as the target eye to be inspected may be determined based on a relative positional relationship between the fundus camera apparatus and the examinee.

Next, the image processing section configured to detect the alignment state between the eye to be inspected and the apparatus main body will be described with reference to FIG. 4.

Similar to the first embodiment, the image processing section according to this embodiment is embedded in the system control section 16.

Figure 4:
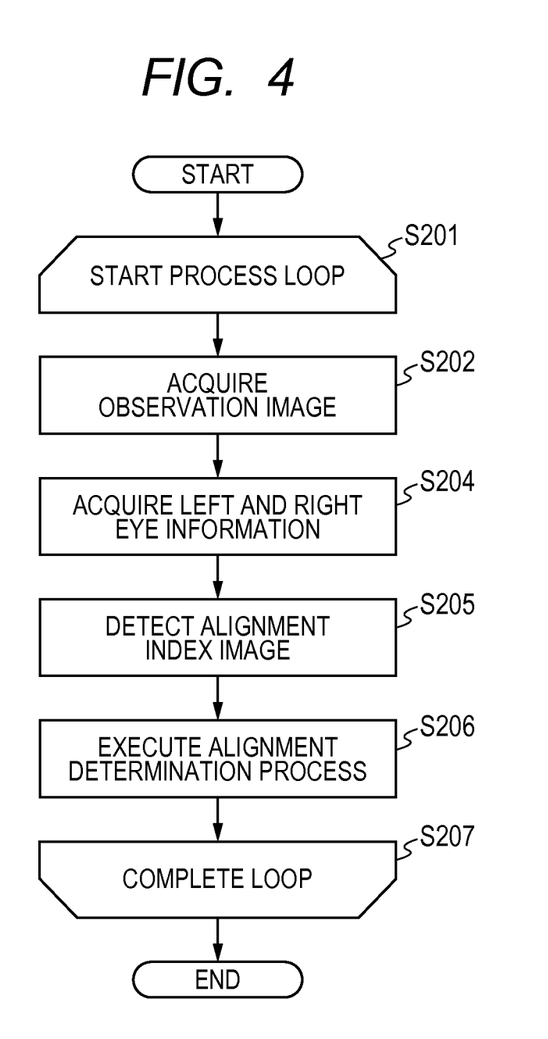
FIG. 4 is a flowchart illustrating an image processing of an alignment detection section according to Second embodiment.

FIG. 4 illustrates an image processing flow of an alignment detection section. In step S201, a process loop starts. First, in step S202, the fundus image processed by the image signal processing section 15 is acquired as an observation image.

In step S204, information about which of the right eye or the left eye is set to as the eye to be inspected is acquired from the manipulation section 18.

Next, in step S205, the alignment index image is detected. In step S206, alignment determination is performed.

Here, when the eye to be inspected is the right eye, the optic papilla is positioned in the right side (nose side). Meanwhile, when the eye to be inspected is the left eye, the optic papilla is positioned in the left side. For this reason, when the alignment index is projected onto the right and left sides of the eye to be inspected, the alignment index image close to the optic papilla is determined as any one of the left or right side. In this case, a module as a detection unit for detecting the right and left sides of the input eye in the image processing section serves as an optic papilla detection unit for detecting the optic papilla position according to the invention.

That is, when the eye to be inspected is the right eye, the alignment index image projected onto the right side and the optic papilla are in a closer positional relationship, and the opposite is true on the left side. Since the alignment index image close to the optic papilla highly likely overlaps with the optic papilla, it is increasingly difficult to accurately detect the alignment index.

For this reason, in step S206, based on information about the left/right sides of the eye to be inspected acquired in step S204, it is determined which one of the alignment index images is used in an alignment determination process, and the alignment determination process is performed.

That is, the alignment determination process is performed such that, when the eye to be inspected is the right eye, alignment determination is performed using the alignment index image in the right side, or when the eye to be inspected is the left eye, alignment determination is performed using an alignment index image in the opposite side.

The alignment determination result is notified to the image signal processing section 15 and is displayed on the display section 17. Based on the alignment result, an operator performs shooting to capture an appropriate image.

As a result, it is possible to shoot the fundus image with higher alignment accuracy.

Third Embodiment

In this embodiment, in the ophthalmologic apparatus according the second embodiment, fixation position information presented to the examinee is used to determine a papilla position.

A fixation optical system used in this embodiment will be described. For example, the fixation optical system is disposed on an optical path in behind of the objective lens 2 facing the eye to be inspected E illustrated in FIG. 1. As the fixation optical system, a relay lens, a liquid crystal plate, and a light source are sequentially disposed in behind of the objective lens 2. The liquid crystal plate is used to allow light from the light source to turn on in an arbitrary position for fixing the eye to be inspected E.

Figure 5:
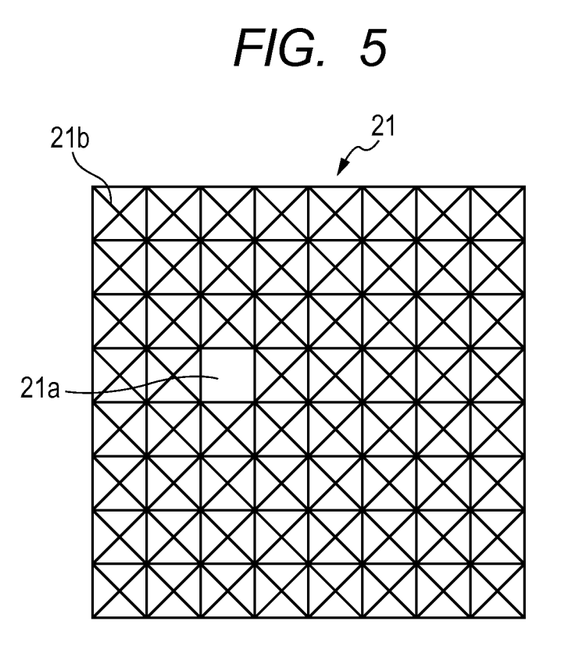
FIG. 5 is a diagram illustrating a positional relationship between a light-shielding portion and an opening portion serving as a fixation target of a liquid crystal plate.

In order to photograph a desired portion of the eye to be inspected E, an operator turns on a desired position of the liquid crystal plate 21. When the desired portion is changed, a lighting position of the liquid crystal plate 21 is moved using a fixation target moving switch, for example, a cross key. A positional relationship between the light-shielding portion 21b and the opening portion 21a serving as a fixation target of the liquid, crystal plate 21 is illustrated in FIG. 5. In the configuration described above, examinee fixation is induced by designating a presentation position of the fixation target.

Figure 6:
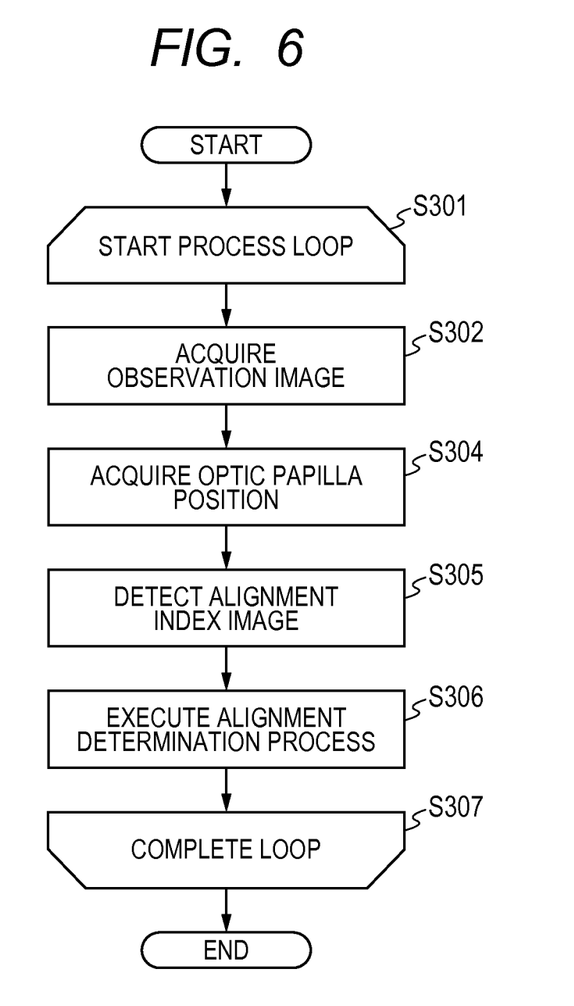
FIG. 6 is a flowchart illustrating an image processing of an alignment detection section according to Embodiment 3.

Next, an image processing flow will be described. FIG. 6 illustrates an image processing flow of the alignment detection section. In step S301, a process loop starts. First, in step S302, the fundus image processed by the image signal processing section 15 is acquired as an observation image.

Figure 8:
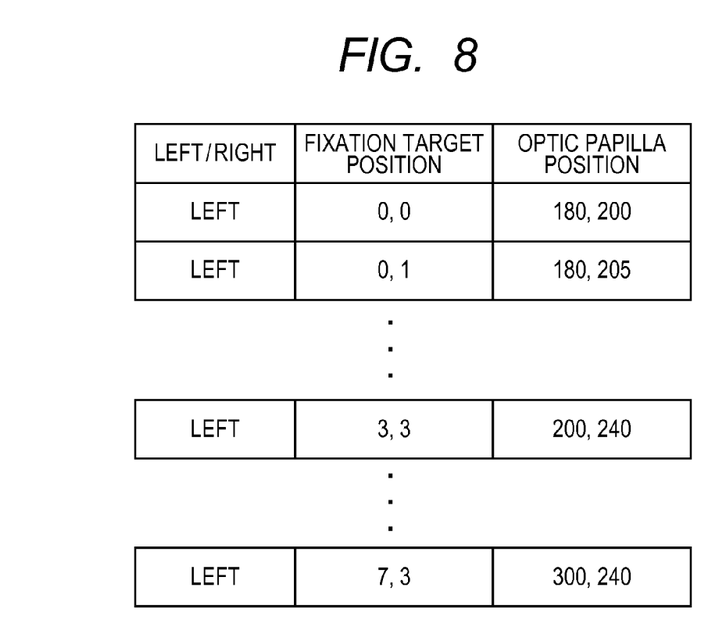
FIG. 8 illustrates an optic papilla position table.

In step S304, an optic papilla position is acquired from an optic papilla position table created in advance as illustrated in FIG. 8. The optic papilla position table is obtained by tabulating estimated optic papilla positions in advance depending on the left/right side of the eye to be inspected and the illuminated fixation target position.

Figure 7:
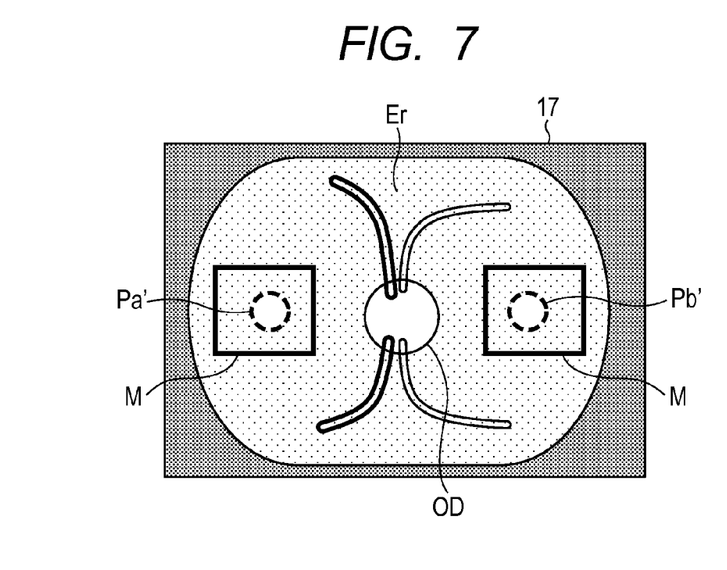
FIG. 7 is a schematic diagram illustrating an image when a fundus is observed.

FIG. 2 is a schematic diagram illustrating the fundus image around a posterior pole serving as a center of the posterior sclera as a representative configuration of the fundus image when the eye to be inspected is the left eye. In this case, an XY position (180, 200) on an estimated image of an optic papilla OD from a fixation target position (3, 3) and information about left/right sides of the eye to be inspected (left) are provided as a table. Since the observation image includes a pixel number of 640×480, the XY position also indicates a position on the image having the pixel number. FIG. 7 is a schematic diagram illustrating the fundus image around the optic papilla. Similarly, in this case, an XY position (300, 240) of the optic papilla estimated from a fixation target position (7, 3) and information about the left/right side of the eye to be inspected (left) are also acquired.

Then, in step S305, the alignment index images Pa' and Pb' are detected. In step S306, alignment determination is performed.

Here, based on a relationship between the optic papilla position acquired in step S304 and the positions of the alignment index images Pa' and Pb' acquired in step S305, it is determined which one of the alignment index images is used for the alignment determination process, and the alignment determination process is performed.

That is, in the fundus image around a posterior pole as a center of a posterior sclera illustrated in FIG. 2, the alignment index image Pa' overlaps with the optic papilla OD. Therefore, the alignment index image Pb' is used for the alignment determination process.

In addition, in the fundus image around the optic papilla illustrated in FIG. 7, both the alignment index images Pa' and Pb' overlap with the optic papilla. Therefore, both images are used for the alignment determination process. Alternatively, any one of the alignment index images may also be used.

The alignment determination result acquired through steps described above is notified to the image signal processing section 15 and is displayed on the display section 17. Based on the alignment result, an operator performs shooting to capture an appropriate image.

That is, according to this embodiment, the optic papilla position detection unit detects the optic papilla position based on the left/right sides of the eye to be inspected and the presentation position of the fixation target for inducing examinee fixation. Alternatively, the optic papilla position detection unit may include an input unit configured to input the optical papilla position and a detection unit configured to detect the optic papilla from the input papilla position.

As a result, it is possible to photograph the fundus image with higher alignment accuracy.

Other Embodiments

In the aforementioned embodiment, the alignment determination result is notified to an operator. Therefore, it is possible to easily perform shooting in a more accurate alignment state. However, the shooting may be automatically performed based on the alignment determination result.

As described above, the alignment between the eye to be inspected and the apparatus is three-dimensionally determined. Due to overlapping between the optic papilla and the alignment index, alignment determination in the Z direction is the most difficult, that is, a distance between the eye to be inspected and the fundus. Therefore, a result of a plurality of alignment index images may be generally used to determine the XY position and only alignment determination in the Z direction may use the determination process of the aforementioned embodiment.

Moreover, the invention may also be implemented by performing the following process. More specifically, software (program) for implementing functions of the aforementioned embodiment is provided to a system or an apparatus via a network or various recording media, and a computer (for example, a CPU or an MPU) in the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application. No. 2012-247025, filed Nov. 9, 2012, which hereby incorporated by reference herein in its entirety.

What is claimed is:

1. An ophthalmologic apparatus comprising:
a projection unit configured to project a plurality of alignment indices onto an eye to be inspected;
an optic papilla position detection unit configured to detect an optic papilla position of the eye to be inspected; and
an alignment detection unit configured to detect a positional relationship between the eye to be inspected and an apparatus main body based on a reflection image of an alignment index of the plurality of alignment indices,
wherein when the reflection image of an alignment index overlaps with the optic papilla, the alignment detection unit performs alignment detection by using the reflection image of at least one alignment index of the plurality of alignment indices other than the alignment index whose reflection image overlaps with the optic papilla.

2. The ophthalmologic apparatus according to claim 1, wherein the optic papilla position detection unit detects the optic papilla from an observation image of a fundus of the eye to be inspected.

3. The ophthalmologic apparatus according to claim 1, wherein the optic papilla position detection unit detects which one of right and left eyes is the eye to be inspected.

4. The ophthalmologic apparatus according to claim 1, wherein the optic papilla position detection unit detects the optic papilla position based on the left/right sides of the eye to be inspected and a presentation position of a fixation target for inducing examinee fixation.

5. The ophthalmologic apparatus according to claim 1, wherein the optic papilla position detection unit detects the optic papilla from the papilla position input from an input unit configured to input a position of the optic papilla.

6. An ophthalmologic imaging method comprising steps of:
detecting an optic papilla position of the eye to be inspected;
projecting a plurality of alignment indices onto an eye to be inspected; and detecting a positional relationship between the eye to be inspected and an apparatus main body based on a reflection image of an alignment index of the plurality of alignment indices, wherein when the reflection image of an alignment index overlaps with the optic papilla, in the detecting of the positional relationship, alignment is detected by using the reflection image of at least one alignment index of the plurality of alignment indices other than the alignment index whose reflection image overlaps with the optic papilla.

7. The ophthalmologic imaging method according to claim 6, wherein, in the detecting of the optic papilla position, the optic papilla is detected from an observation image of a fundus of the eye to be inspected.

8. The ophthalmologic imaging method according to claim 6, wherein, in the detecting of the optic papilla position, it is detected which one of right and left eyes is the eye to be inspected.

9. The ophthalmologic imaging method according to claim 6, wherein, in the detecting of the optic papilla position, the optic papilla position is detected based on the left/right sides of the eye to be inspected and a presentation position of a fixation target for inducing examinee fixation.

10. The ophthalmologic imaging method according to claim 6, wherein, the detecting of the optic papilla position includes inputting a position of the optic papilla and detecting the optic papilla from the input papilla position.

11. A program causing a computer to execute each operation of the ophthalmologic imaging method according to claim 6.

12. The ophthalmologic apparatus comprising:
a projection unit configured to project a plurality of alignment indices onto an eye to be inspected;
an optic papilla position detection unit configured to detect an optic papilla position of the eye to be inspected; and
an alignment detection unit configured to detect a positional relationship between the eye to be inspected and an apparatus main body based on a reflection image of an alignment index of the plurality of alignment indices,
wherein the plurality of alignment indices includes a first index and a second index, and
wherein when a first reflection image of the first index overlaps with the optic papilla, the alignment detection unit uses a second reflection image of the second index, and when neither of the first reflection image and the second reflection images overlap with the optic papilla, the alignment detection unit uses both the first reflection image and the second reflection image.

13. The ophthalmologic apparatus according to claim 1, wherein the projection unit stops projecting the plurality of alignment indices onto the eye to be inspected when the optic papilla position detection unit detects the optic papilla position.

14. The ophthalmologic imaging method according to claim 6, wherein the plurality of alignment indices includes a first index and a second index, and
wherein detecting of the positional relationship uses one of a first reflection image of the first index and a second reflection image of the second index, or uses both the first reflection image and the second reflection image.

* * * * *